United States Patent
Back et al.

(10) Patent No.: US 11,773,053 B2
(45) Date of Patent: Oct. 3, 2023

(54) CATIONIC QUATERNARY AMMONIUM COMPOUNDS AND COMPOSITIONS COMPRISING SAME AND PROCESSES FOR THEIR MANUFACTURE

(71) Applicant: RHODIA OPERATIONS, Aubervilliers (FR)

(72) Inventors: Olivier Back, Lyons (FR); Bing Hong, Shanghai (CN); Matthieu Guirardel, Bordeaux (FR)

(73) Assignee: RHODIA OPERATIONS, Lyons (FR)

( * ) Notice: Subject to any disclaimer, the term of this patent is extended or adjusted under 35 U.S.C. 154(b) by 291 days.

(21) Appl. No.: 16/769,845

(22) PCT Filed: Dec. 20, 2017

(86) PCT No.: PCT/CN2017/117432
§ 371 (c)(1),
(2) Date: Jun. 4, 2020

(87) PCT Pub. No.: WO2019/119293
PCT Pub. Date: Jun. 27, 2019

(65) Prior Publication Data
US 2020/0392070 A1 Dec. 17, 2020

(51) Int. Cl.
*C07C 211/63* (2006.01)
*C02F 1/52* (2023.01)
*C02F 1/54* (2023.01)
*C07C 209/68* (2006.01)

(52) U.S. Cl.
CPC .......... *C07C 211/63* (2013.01); *C02F 1/5272* (2013.01); *C02F 1/547* (2013.01); *C07C 209/68* (2013.01)

(58) Field of Classification Search
CPC ... C07C 211/63; C07C 209/68; C02F 1/5272; C02F 1/547
See application file for complete search history.

(56) References Cited

U.S. PATENT DOCUMENTS

| | | | | |
|---|---|---|---|---|
| 2,981,731 A * | 4/1961 | Moore et al. | ........ | C07D 499/00 546/61 |
| 3,053,894 A * | 9/1962 | Van Dijk | ............... | C07C 211/21 564/453 |
| 3,729,564 A * | 4/1973 | Chang et al. | ........ | C07D 263/52 514/183 |
| 9,636,302 B2 * | 5/2017 | Constien | ............... | C07D 241/04 |
| 11,028,315 B2 * | 6/2021 | Back | ........................ | E21B 43/16 |
| 11,186,538 B2 * | 11/2021 | Back | ........................ | A01N 25/30 |
| 11,198,669 B2 * | 12/2021 | Wu | ............................. | C25B 3/09 |
| 2012/0295832 A1 * | 11/2012 | Constien | ............... | A61K 31/713 514/23 |
| 2022/0306570 A1 * | 9/2022 | Back | ........................ | C11D 1/62 |

FOREIGN PATENT DOCUMENTS

| | | | | |
|---|---|---|---|---|
| CN | 102531928 A | | 7/2012 | |
| CN | 104086511 A | | 10/2014 | |
| CN | 107162918 A | * | 9/2017 | .......... B01F 17/0042 |
| CN | 107162918 A | | 9/2017 | |
| DE | 2216098 A1 | | 10/1973 | |
| EP | 235942 A | * | 9/1987 | .......... C07D 295/13 |
| GB | 898928 | * | 6/1962 | |
| GB | 1277947 A | * | 6/1972 | ............. A01N 33/04 |
| JP | 2010052249 A | | 3/2010 | |
| WO | WO-2013059496 A1 | * | 4/2013 | .......... A61K 31/713 |
| WO | 2013148613 A1 | | 10/2013 | |
| WO | WO-2013148613 A1 | * | 10/2013 | ............. A61K 8/416 |
| WO | 2017174424 A1 | | 10/2017 | |
| WO | WO-2017174424 A1 | * | 10/2017 | .......... C07C 229/12 |
| WO | WO-2018087188 A1 | * | 5/2018 | ............. A01N 25/30 |

OTHER PUBLICATIONS

N. Brovtsyna et al., 152 Journal of Membrane Biology, 77-87 (1996) (Year: 1996).*
CAS Abstract of R. Shepherd et al., 5 Journal of Medicinal & Pharmaceutical Chemistry, 823-835 (1962) (Year: 1962).*
CAS Abstract M. Masaki et al., EP 0235942 (1987) (Year: 1987).*
R. Shepherd et al., 5 Journal of Medicinal & Pharmaceutical Chemistry, 823-835 (1962) (Year: 1962).*
J. March, Advanced Organic Chemistry Reactions, Mechanisms and Structure 248-272 (4th ed., 1992) (Year: 1992).*
Oikonomou, et al., "Fabric Softener-Cellulose Nanocrystal Interaction: A Model for Assessing Surface Deposition on Cotton", The Journal of Physical Chemistry, B 2017, 121, 10, pp. 2299-2307.
Kitatsuji, et al., "Studies on the Components in NTU (Nevada-Texas-Utah) Shale Oil. IV. 1) The Hofmann Degradation of Open-Chain Quaternary Ammonium Compounds", Yakugaku Zasshi, 1971, vol. 91, issue 7, pp. 732-737.

* cited by examiner

*Primary Examiner* — Alexander R Pagano
(74) *Attorney, Agent, or Firm* — Osha Bergman Watanabe & Burton LLP

(57) ABSTRACT

The present invention concerns new cationic quaternary ammonium compounds which exhibit excellent adsorption properties on negatively charged surfaces. These ones can notably be obtained firstly by reacting an internal ketone with a twin-tail amine under reductive amination conditions to obtain a twin tail triamine, then subjecting the twin tail triamine to a quaternization reaction. They can also obtained be obtained by the quaternization reaction of a certain diamine.

11 Claims, No Drawings

CATIONIC QUATERNARY AMMONIUM COMPOUNDS AND COMPOSITIONS COMPRISING SAME AND PROCESSES FOR THEIR MANUFACTURE

This application is a U.S. national stage entry under 35 U.S.C. § 371 of International Application No. PCT/CN2017/117432, filed on Dec. 20, 2017, the entire content of which is explicitly incorporated herein by this reference.

The present invention relates to new cationic quaternary ammonium compounds and compositions comprising same and processes for their preparation.

Quaternary ammonium compounds are used in various applications as surfactants.

BACKGROUND OF THE TECHNOLOGY

Surfactants are compounds that lower the surface tension (or interfacial tension) between two liquids, a liquid and a gas or between a liquid and a solid. Surfactants may act as detergents, wetting agents, emulsifiers, foaming agents, and dispersants.

Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

DE 22 16 098 discloses quaternary ammonium compounds of the general formula

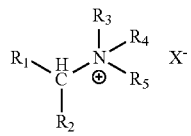

in which $R_1$ and $R_2$ are aliphatic residues with 15-43 carbon atoms and $R_3$ to $R_5$ are alkyl groups with 1 to 3 carbon atoms.

WO 2017/0174424 discloses zwitterionic compounds of formula

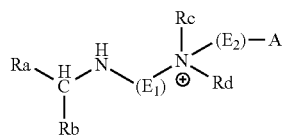

wherein each of $R_a$ and $R_b$ is a linear or branched hydrocarbon chain, each of $R_c$ and $R_d$ is a linear or branched hydrocarbon chain having 1 to 10 carbon atoms, each of $E_1$ and $E_2$ is a divalent linear or branched hydrocarbon radical and A is a carboxylate group or a sulfonate group. The compounds are useful for enhanced oil recovery purposes.

It was an object of the present invention to provide new compounds which may i.a. be used as surfactants, e.g. for use as flocculants and which show improved properties in this regard.

This object has been achieved with the compounds of formula (I) to (IV) in accordance with claim 1.

Preferred embodiments of the compounds in accordance with the present invention are set forth in the dependent claims and in the detailed specification hereinafter.

A further embodiment of the present invention relates to compositions comprising compounds of formula (II) in combination with at least one compound of formula (III) and/or (IV).

A still further embodiment of the present invention relates to processes for the manufacture of the compounds and compositions in accordance with the present invention.

DETAILED DESCRIPTION OF THE INVENTION

The compounds according to the present invention are represented by formulae (I) to (IV)

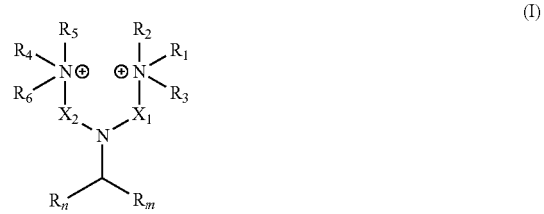
(I)

(II)

(III)

(IV)

wherein $R_n$ and $R_m$ independently represent a $C_3$-$C_{27}$ aliphatic group, $R_1$ to $R_6$ and $R_9$ to $R_{14}$, which may be the same or different at each occurrence, represent hydrogen or a $C_1$-$C_8$ alkyl group or wherein a pair of substituents selected from $R_1$, $R_2$ and $R_3$ in formula (I) or (II) or from $R_4$, $R_5$ and $R_6$ in formula (I) or from $R_9$, $R_{10}$ and $R_{11}$ in formula (III) or from $R_{12}$, $R_{13}$ and $R_{14}$ in formula (IV) may form a divalent hydrocarbon radical with 2 to 6 carbon atoms thereby forming a ring structure with the nitrogen atom to which they are attached, $R_7$, $R_8$ and $R_{15}$, which may be the same or different at each occurrence, are hydrogen or a $C_1$-$C_8$ alkyl group, or $R_7$ and $R_8$ in formula (II) may form a divalent hydrocarbon radical with 2 to 6 carbon atoms thereby forming a ring structure with the nitrogen atom to which they are attached and $X_1$ and $X_2$, which may be the same or different at each occurrence, represent a linear or branched divalent hydrocarbon radical with 1 to 24 carbon atoms which can be optionally substituted and/or interrupted by one or more heteroatoms or heteroatom containing groups.

$R_n$ and $R_m$ represent a $C_3$-$C_{27}$ aliphatic group, very often a $C_3$-$C_{19}$ aliphatic group, often a aliphatic $C_7$-$C_{17}$ group.

The number of carbon atoms of $R_n$ and $R_m$ can be even or odd numbers. $R_n$ and $R_m$ may be identical to each other or, alternatively, $R_n$ and $R_m$ may differ from each other.

The number of carbon atoms of $R_n$ and of $R_m$, as herein represented by the couple (n,m), can be notably any of the following couples:

(3,3), (5,5), (7,7), (9,9), (11,11), (13,13), (15,15), (17,17), (19,19), (21,21), (23,23), (25,25), (27, 27)

(7,9), (7,11), (7,13), (7,15), (7,17), (7,19), (7,21), (7,23), (7,25), (7,27)

(9,11), (9,13), (9,15), (9,17), (9,19), (9,21), (9,23), (9,25), (9,27)

(11,13), (11,15), (11,17), (11,19), (11,21), (11,23), (11, 25), (11,27)

(13,15), (13,17), (13,19), (13,21), (13,23), (13,25), (13, 27)

(15,17), (15,19), (15,21), (15,23), (15,25), (15,27)

(17,19), (17,21), (17,23), (17,25), (17,27)

(19,21), (19,23), (19,25), (19,27)

(21,23), (21,25), (21,27)

(23,25), (23,27) or (25,27).

The aliphatic groups $R_n$ and $R_m$ may be linear or branched.

The aliphatic groups $R_n$ and $R_m$ may be free of any double bond and of any triple bond. Alternatively, the aliphatic groups $R_n$ and $R_m$ may comprise at least one —C═C— double bond and/or at least one —C≡C— triple bond.

The aliphatic groups $R_n$ and $R_m$ are advantageously chosen from alkyl groups, alkenyl groups, alkanedienyl groups, alkanetrienyl groups and alkylnyl groups.

Preferably, the aliphatic groups $R_n$ and $R_m$ are independently chosen from alkyl and alkenyl groups.

More preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from (i) $C_6$-$C_{17}$ alkyl and $C_6$-$C_{17}$ alkenyl groups or from (ii) $C_7$-$C_{17}$ alkyl and $C_7$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group or a $C_7$-$C_{17}$ alkyl group.

$R_1$ to $R_6$ and $R_9$ to $R_{14}$, which may be the same or different at each occurrence in the compounds in accordance with the present invention, represent hydrogen or a $C_1$-$C_8$ alkyl group, preferably an alkyl group having from 1 to 6 carbon atoms and in particular may be methyl, ethyl, propyl, isopropyl, n-butyl, iso-butyl, or tert-butyl. In accordance with a particularly preferred embodiment $R_1$ to $R_6$ and $R_9$ to $R_{14}$ are methyl. If $R_1$ to $R_6$ and $R_9$ to $R_{14}$ are alkyl groups, they may be linear or branched.

A pair of substituents selected from $R_1$, $R_2$ and $R_3$ in formula (I) or (II) or from $R_4$, $R_5$ and $R_6$ in formula (I) or from $R_9$, $R_{10}$ and $R_{11}$ in formula (III) or from $R_{12}$, $R_{13}$ and $R_{14}$ in formula (IV) may form a divalent hydrocarbon radical with 2 to 6 carbon atoms thereby forming a ring structure with the nitrogen atom to which they are attached. The divalent hydrocarbon radical may preferably be an alkylene group —[(CH$_2$)$_2$]p with p being an integer of from 4 to 5.

$R_7$, $R_8$ and $R_{15}$, which may be the same or different at each occurrence, represent a group selected from hydrogen or a $C_1$-$C_8$ alkyl group, preferably an alkyl group having from 1 to 6 carbon atoms and in particular may be methyl, ethyl, propyl, isopropyl, n-butyl, iso-butyl, or tert-butyl. In accordance with a particularly preferred embodiment $R_7$ to $R_8$ are methyl. If $R_7$, $R_8$ and $R_{15}$ are alkyl groups, they may be linear or branched.

Substituents $R_7$, $R_8$ may form a divalent hydrocarbon radical with 2 to 6 carbon atoms thereby forming a ring structure with the nitrogen atom to which they are attached. The divalent hydrocarbon radical may preferably be an alkylene group —[(CH$_2$)$_2$]p with p being an integer of from 4 to 5.

A first group of preferred compounds in accordance with the present invention are compounds of formula (I) or (II) wherein $X_1$ and $X_2$ are (—CH$_2$—)$_m$ with m being an integer equal to 2 to 20 and $R_1$ to $R_8$ are hydrogen or an alkyl group with 1 to 6 carbon atoms.

Another group of preferred compounds in accordance with the present invention are compounds of formula (I) or (II) wherein $X_1$ and $X_2$ are —(CH$_2$)$_3$— and $R_1$ to $R_8$ are methyl.

Still another group of preferred compounds in accordance with the present invention are compounds of formula (I) or (II) wherein $X_1$ and $X_2$ are a branched divalent hydrocarbon group, which may be optionally substituted and/or interrupted by one or more heteroatoms or heteroatom containing groups and $R_1$ to $R_8$ are as defined in claim 1.

Yet another group of preferred compounds in accordance with the present invention are compounds of formula (I) or (II) wherein $X_1$ and $X_2$ are a linear or branched divalent hydrocarbon group substituted and/or interrupted by one or more heteroatoms or heteroatom containing groups and $R_1$ to $R_8$ are as defined in claim 1.

Still another group of preferred compounds in accordance with the present invention are compounds of formula (II) wherein $X_1$ and $X_2$ are an aliphatic divalent group containing 2 to 20 carbon atoms with the exception of —(CH$_2$)$_3$— and $R_1$ to $R_3$, $R_7$ and $R_8$ are as defined in claim 1.

Still another group of preferred compounds in accordance with the present invention are compounds of formula (I) or (II) wherein $X_1$, $X_2$, $R_n$, and $R_m$ are as defined in claim 1 and $R_1$ to $R_8$ are a $C_2$-$C_8$ alkyl group.

Compounds of formula (III) and formula (IV) have not been described before and constitute another embodiment of the present invention. What has been said above for preferred meanings for the substituents $R_1$ to $R_8$, $X_1$ and $X_2$ applies in the same manner to substituents $R_9$ to $R_{15}$ and $X_1$ and $X_2$ in the compounds of formulae (III) and (IV) so that reference is made here to the foregoing description to avoid unnecessary repetitions.

A further embodiment of the present invention thus relates to compounds of formula (III) or (IV) wherein $R_9$ to $R_{14}$, which may be the same or different at each occurrence, represent hydrogen or a $C_1$-$C_8$ alkyl group or wherein a pair of substituents selected $R_9$, $R_{10}$ and $R_{11}$ in formula (III) or from $R_{12}$, $R_{13}$ and $R_{14}$ in formula (IV) may form a divalent hydrocarbon radical with 2 to 6 carbon atoms, preferably an alkylene group [—(CH$_2$)$_p$] with p being an integer of from 4 to 5, thereby forming a ring structure with the nitrogen atom to which they are attached, $R_{15}$ is hydrogen or a $C_1$-$C_8$ alkyl group and $X_1$ and $X_2$, which may be the same or different at each occurrence, represent a linear or branched divalent hydrocarbon radical with 1 to 24 carbon atoms which can be optionally substituted and/or interrupted by one or more heteroatoms or heteroatom containing groups.

Compounds of formula (I) to (IV) wherein $R_m$ and $R_n$ differ from each other can be obtained by using a mixture of fatty acids having different chain lengths as starting materials. For example, using a mixture of two fatty acids $R_m$—COOH and $R_n$—COOH with m≠n, a mixture comprising a first compound (I), (II), (III) or (IV) with aliphatic groups ($R_m$, $R_m$), a second compound with aliphatic groups ($R_m$, $R_n$) and a third compound with aliphatic groups ($R_n$, $R_n$) is generally obtained, and the compounds of the so-obtained mixture can then be optionally separated using common separation techniques that are well known to the skilled person. More generally, when using N fatty acids having different chain lengths, wherein N is an integer greater than or equal to 2, a mixture comprising (N+$C_N^2$) compounds of formula (I), (II), (III) or (IV) is generally obtained, wherein $$C_N^2 = \tfrac{1}{2} \cdot N!/(N-2)!$$

Hence, an aspect of the present invention relates to a mixture comprising (N+$C_N^2$) compounds of formula (I) wherein N is an integer greater than or equal to 2 (for example, N can be from 2 to 20). Another aspect of the present invention relates to a mixture comprising (N+$C_N^2$) compounds of formula (II) wherein N is an integer greater than or equal to 2 (for example, N can be from 2 to 20). Still another aspect of the present invention relates to a mixture comprising (N+$C_N^2$) compounds of formula (III) wherein N is an integer greater than or equal to 2 (for example, N can be from 2 to 20). Yes another aspect of the present invention relates to a mixture comprising (N+$C_N^2$) compounds of formula (IV) wherein N is an integer greater than or equal to 2 (for example, N can be from 2 to 20).

A further embodiment of the present invention are compositions comprising compounds of formula (II) and, in addition, at least one of compounds of formula (III) and/or (IV), preferably compositions comprising at least one compound of formula (II), at least one compound of formula (III) and at least one compound of formula (IV).

Preferred compositions in accordance with the present invention comprise 1-97 mol % of a compound of formula (II), 1 to 97 mol % of a compound of formula (III) and the remainder to 100 mol % of a compound of formula (IV).

The compounds of formula (II), (III) and (IV) can e.g. be obtained by the quaternization reaction of compounds of formula (VIII).

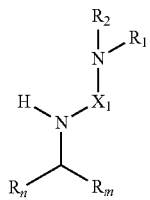
(VIII)

wherein $R_n$, $R_m$, $R_1$, $R_2$ and $X_1$ have the meaning as defined in claim 1, or by mixing the individual compounds in accordance with the desired mixture ratio.

Preferably the compositions are obtained through quaternization of a compound of formula (VIII) and the reaction mixture may used as such or the reaction mixture may be subjected to further treatment to modify and adjust the ratio of the compounds of formula (II), (III) and (IV).

In accordance with a first process in accordance with the present invention, the compounds of formula (I) are obtained by a process wherein an internal ketone K1 of formula (V), which can be obtained by a process P of decarboxylative ketonization, is reacted in a first step with a twin-tail amine of formula (VI), which is a triamine, under reductive amination conditions to obtain a twin tail triamine of formula (VII) in accordance with the following general reaction scheme

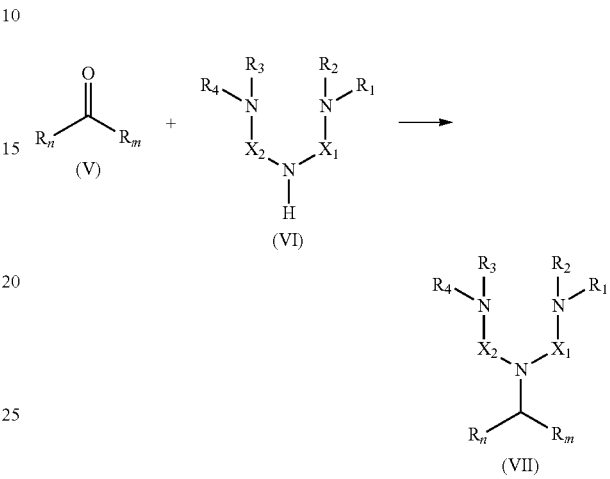

wherein
$R_n$, $R_m$, $X_1$, $X_2$ and $R_1$ to $R_4$ in the above scheme have the meanings as defined above for the compounds in accordance with the present invention, followed by a second step in which the reaction product (VII) obtained in the first step is quaternized to obtain the bicationic quaternary ammonium compound of formula (I).

The amination reaction in the first step is preferably performed by reacting the ketone (V) and the amine (VI) in the presence of a transition metal (e.g. Ni, Co, Cu, Fe, Rh, Ru, Ir, Pd, Pt) based catalyst (typically Pd/C), in an autoclave under hydrogen pressure (typically from 100 kPa to 20 MPa).

An internal ketone is generally a compound of formula (V)

(V)

wherein $R_n$ and $R_m$ independently represent an aliphatic group, generally a $C_3$-$C_{27}$ aliphatic group, very often a $C_3$-$C_{19}$ aliphatic group, often an aliphatic $C_6$-$C_{17}$ group or $C_7$-$C_{17}$ group.

Preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often either from $C_6$-$C_{17}$ alkyl and $C_6$-$C_{17}$ alkenyl groups or from $C_7$-$C_{17}$ alkyl and $C_7$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group or $C_7$-$C_{17}$ alkyl group.

According to a possible embodiment, the first reaction step to obtain the compound of formula (VII) is carried out in a solvent. However, the presence of such solvent is not compulsory and according to a specific embodiment, no solvent is used for this step. The exact nature of the solvent, if any, may be determined by the skilled person. Typical suitable solvents include, without limitation, methanol, ethanol, isopropanol, tert-butanol, THF, 2-methyltetrahydrofuran, 1,4-dioxane, dimethoxyethane, diglyme and mixtures thereof.

Besides, the amination is usually carried out at a temperature ranging from 15° C. to 400° C. and may be conducted batchwise, semi-continuously or continuously and generally performed either in a batch mode or in a continuous mode using a fixed-bed catalyst (gas-solid or gas-liquid-solid process).

Preferred amines of formula (VI) are amines where $X_1$ and $X_2$ are —$CH_2$—$CH_2$— or —$(CH_2)_m$— wherein m is an integer from 3 to 20 and $R_1$ to $R_4$ independently represent hydrogen or an alkyl group having 1 to 6 carbon atoms (such as e.g. —$CH_3$, —$CH_2CH_3$, propyl or isopropyl).

A particularly preferred amine is 3,3'-iminobis(N,N-dimethylpropylamine)

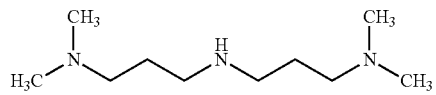

Preferably, the process of the invention as described above can be used for the preparation of the preferred groups of compounds of formula (I) described and defined above, i.e. for compounds of formula (I) wherein $X_1$ and $X_2$ are —$(CH_2)_m$— with m being an integer equal to 2 to 20 and $R_1$ to $R_6$ are hydrogen or an alkyl group with 1 to 6 carbon atoms or wherein $X_1$ and $X_2$ are —$(CH_2)_3$— and $R_1$ to $R_6$ are methyl.

The first step described above may also be preferably used for the synthesis of compounds of formula (I) wherein $X_1$ and $X_2$ are a branched divalent hydrocarbon group, which may be optionally substituted and/or interrupted by one or more heteroatoms or heteroatom containing groups and $R_1$ to $R_6$ are as defined in claim 1 or wherein $X_1$ and $X_2$ are a branched or linear divalent hydrocarbon group substituted and/or interrupted by one or more heteroatoms or heteroatom containing groups and $R_1$ to $R_6$ are as defined in claim 1.

In accordance with a first preferred embodiment of the first step of the process in accordance with the present invention for the preparation of compounds of formula (I) said process comprises a step wherein the internal ketone K1 of formula (V) is synthesized by a process P of decarboxylative ketonization reaction of a fatty acid, a fatty acid derivative or a mixture thereof in a liquid phase with a metal compound as catalyst in a reaction medium, said process P being characterized in that a ketone K2 at liquid state, which is identical or similar to the internal ketone K1, is introduced into the reaction medium.

Suitable metals for use in the process P in the process of the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, carboxylate salts of the aforementioned metals, naphthenate salts of the aforementioned metals or acetate salts of the aforementioned metals, preferably metal compounds are oxides of the aforementioned metals. Magnesium, iron, and their oxides, are particularly preferred as metal compounds In accordance with a preferred embodiment the metal compound is iron(II) oxide or iron(III) oxide or a mixed oxide of iron(II) and iron (III) such as e.g. FeO, $Fe_3O_4$ or $Fe_2O_3$. Iron powder has economical advantages as it is cheap and abundantly available. It has been observed that iron oxides are efficient to promote the reaction reducing the overall reaction times.

The catalysis of the reaction may be qualified as a homogeneous catalysis since in the reaction conditions an intermediate metal carboxylate salt (e.g. iron carboxylate) is formed through the initial reaction between the fatty acid or its derivative with the metal compound and this intermediate salt is substantially soluble in the reaction medium.

The process P in accordance with a first embodiment is characterized in that a ketone K2 at liquid state is introduced into a reactor.

The ketone K2 may be identical or similar to the internal ketone K1 to be synthesized.

The ketone K2 has usually a high boiling point, preferably a boiling point of at least 270° C., more preferably at least 290° C., even more preferably at least 310° C. As herein used, the term "boiling point" generally denotes the normal boiling point (also called the atmospheric boiling point or the atmospheric pressure boiling point) of a liquid; it corresponds to the case in which the vapor pressure of the liquid equals the defined atmospheric pressure at sea level, 1 atmosphere. It can be measured by differential scanning calorimetry using for example a METTLER Toledo equipment.

By "a ketone K2 similar to the internal ketone K1", it is to be understood that the difference between the boiling point of the internal ketone K1 and the boiling point of the ketone K2 is equal to or lower than 80° C. Preferably, the difference between the boiling point of the internal ketone K1 and the boiling point of the ketone K2 is equal to or lower than 40° C., preferably equal to or lower than 10° C., more preferably equal to or lower than 5° C., even more preferably equal to or lower than 3° C.

Non limitative examples of ketones suitable as ketone K2 in accordance with process P are 2,2,4,4-tetramethyl-3-pentanone (bp: 152-153° C.), 5-nonanone (bp: 186-187° C.), 8-pentadecanone (bp: 293° C.), heptadecan-8-one (bp: 323° C.), 10-nonadecanone (bp: 335° C.), 12-tricosanone (bp: 404.5° C.), 14-heptacosanone (bp: 454° C.), 16-hentriacontanone (bp: 499.5° C.), 18-pentatriacontanone (bp: 542.5° C.), methyl isobutyl ketone (bp: 117-118° C.), 4-methyl-3-penten-2-one (bp: 130° C.), di isobutyl ketone (bp: 165-170° C.), methyl levulinate (bp: 193-195° C.), trans,trans dibenzylideneacetone (bp: 401° C.), anthraquinone (bp: 379-381° C.), benzophenone (bp: 305° C.), benzoine (bp: 343° C.), acetophenone (bp: 202° C.) and propiophenone (bp: 218° C.).

The ketone K2 is advantageously an internal ketone. The ketone K2 is preferably one or more ketone(s) selected from internal ketones K1 susceptible of being synthesized by the process P, more preferably one or more ketone(s) selected from internal ketones K1 synthesized by the process P. Besides, the ketone K2 introduced into the reaction medium is advantageously one or more ketone(s) selected from ketones having from 7 to 35 carbon atoms, preferably from 15 to 35 carbon atoms. Finally, the ketone K2 introduced into the reaction medium is advantageously one or more ketone(s) selected from aliphatic ketones.

The ketone K2 may consist of one and only one ketone or may be a mixture of ketones. The ketone K2 may be a single ketone or a mixture of ketones wherein the ketone(s) is/are susceptible of being obtained by decarboxylative ketonization reaction of a fatty acid, a fatty acid derivative or a mixture thereof. The ketone K2 may be one and only one ketone or a mixture of ketones wherein the ketone(s) has/have been obtained by decarboxylative ketonization reaction of a fatty acid, a fatty acid derivative or a mixture thereof.

When ketone K2 is a mixture of ketones, said mixture may be homogeneous (i.e. uniform in composition) or heterogeneous; it is preferably homogeneous. When ketone K2 is a mixture of ketones, the ketones of which the mixture is composed are generally at least partially miscible with each other; they are preferably fully miscible with each other. When ketone K2 is a mixture of ketones, said mixture of ketones has advantageously one and only one boiling point. In case of a mixture of ketones, the expression "boiling point of the ketone" is to be understood as the boiling point of the mixture of ketones when said mixture of ketones has one and only one boiling point and as the lowest boiling point of the mixture of ketones when said mixture of ketones has several boiling points.

Preferably, the ketone K2 is a mixture of ketones.

According to an embodiment, the ketone K2 introduced originates from a previous process P for synthesizing a ketone by decarboxylative ketonization reaction of a fatty acid, a fatty acid derivative or a mixture thereof, said previous process P being preferably identical to the process P. In such an embodiment, wherein the fatty acid(s)/fatty acid derivatives(s) for producing the ketone K2 is identical to the fatty acid(s)/fatty acid(s) derivative(s) used in step b) of the process P of the invention, the ketone K2 will be very similar or identical to the internal ketone K1.

According to an embodiment of the invention, water formed during the process P is continuously removed from the reaction medium.

According to an embodiment, the reaction medium of process P is substantially free of third solvents.

The term "fatty acid" refers to a carboxylic acid containing at least 4 carbon atoms; besides, a fatty acid contains generally at most 28 carbon atoms. The term "fatty acid derivative" refers to an anhydride made by the condensation of 2 fatty acids or to an ester made by the condensation of a fatty acid with an alcohol.

Suitable fatty acid derivatives are esters and anhydrides of fatty acids, but the use of the free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional steps and costs. However, if esters are derived from lower alcohols such as for example methanol, ethanol, propanol or butanol, the alcohols may be removed progressively over the course of the reaction e.g. by reactive distillation.

The fatty acids or fatty acid derivatives can be used in the form of so called fatty acids or fatty acid derivatives cuts which may be obtained by the hydrolysis or alcoholysis of different natural fats and oils. Accordingly these cuts may contain various amounts of different linear fatty acids or linear fatty acid derivatives with different chain lengths. Just by way of examples, fatty acid cuts obtained from coconut oil and comprising mainly $C_{12}$-$C_{18}$ fatty acids may be mentioned here. The skilled person is well aware of other fatty acid cuts obtainable form various sources and will select the best suitable starting materials based on the desired ketones.

According to an embodiment of process P, fatty acids having 12 carbon atoms or less, preferably of from 8 to 12 carbon atoms or derivatives of such acids (esters or anhydrides) constitute at least 10 mol % and preferably at least 15 mol % of the entire molar amount of a fatty acid mixture or fatty acid derivative mixture used as starting material. These acids lead to ketones having a total carbon number of 23 or less which have proved to be advantageous in a number of applications. There is no specific upper limit for the amount of these fatty acids or fatty acid derivatives of acids having 12 carbon atoms or less, i.e. the starting material may also entirely consist of such fatty acids and/or such fatty acid derivatives.

Subject to the above, preferred fatty acids for use in the process P are hexanoic acid, isostearic acid, caprylic acid, capric acid, lauric acid, myristic acid, palmitic acid, stearic acid, arachidic acid, behenic acid, lignoceric acid, cerotic acid or mixtures thereof, and preferred fatty acid derivatives are the esters and anhydrides of these acids.

The fatty acids may be free of any —C=C— double bond of and of any —C≡C— triple bond. Non limitative examples of such fatty acids are the previously cited caprylic acid, capric acid, lauric acid, myristic acid, palmitic acid, stearic acid and mixtures thereof.

Alternatively, the fatty acids may comprise one or more double bonds and/or one or more triple bonds. Examples of fatty acids comprising one or more double bonds are oleic acid, linoleic acid, linolenic acid, erucic acid, palmitoleic acid, ricinoleic acid and mixtures thereof. Examples of fatty acids comprising one or more triple bonds are tariric acid, santalbic acid (which also comprises one double bond) and mixtures thereof.

When starting from a single fatty acid, a single symmetrical ketone is obtained as the reaction product; when starting from a cut of fatty acids as described above all the ketones formed by the combination of the different alkyl groups of the starting acids are obtained and the distribution of the different mixed ketones generally follows a statistical binomial law. The reaction equation can be summarized as follows: $R_n$—COOH+$R_m$—COOH→$R_n$—C(=O)—$R_m$+$CO_2$+$H_2O$ wherein $R_n$ and $R_m$ represent the aliphatic, e.g. alkyl, groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$.

The ketone K1 that is synthetized during the process P is an internal ketone.

According to an embodiment, the total amount of fatty acid material (fatty acid plus fatty acid derivative) added in the reaction medium for the decarboxylative ketonization reaction is such that the overall molar ratio of metal to carboxylic groups is in the range of from 1:6 to 1:99, i.e. the amount of metal is about 1 mol % to about 14 mol % and preferably of from 2 to about 10 mol % of the entire amount of fatty acid and fatty acid derivative.

For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P over the prior art.

During the decarboxylative ketonization reaction, the temperature of the reaction medium inside the reactor may be maintained at high temperature, for example the temperature inside the reactor may range from 270° C. to 400° C., preferably from 285 to 350° C., more preferably from 300 to 350° C. The reaction medium may be maintained at high temperature until full conversion of fatty acid and disappearance of the optionally formed intermediate metallic salts.

The process P is preferably carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

During the process P, a reaction medium comprising:
at least part of a ketone K2
at least part of the metal compound, and
at least part of the fatty acid, fatty acid derivative or mixture thereof, may be obtained.

According to a particular embodiment the process P comprises the steps of:

S1) introducing at least part of the ketone K2 at liquid state, at least part of the metal compound, at least part of the fatty acid, fatty acid derivative or mixture thereof into a reactor in order to synthesize the internal ketone K1, said reactor optionally containing, before said introduction, a part of the metal compound, a part of the fatty acid, fatty acid derivative or mixture thereof, a part of the ketone K2 and/or a part of the internal ketone K1, S2) recovering the internal ketone K1 together with the ketone K2, S3) optionally recycling at least part of the internal ketone K1 and ketone K2 and/or at least part of the metal compound to the first step S1.

The reaction medium may be formed in the reactor by introducing the different compounds at the first step S1 according to any introduction policy.

According to a preferred embodiment, the metal compound is not mixed with the fatty acid or fatty acid derivative or mixture thereof before introduction into the reactor, in order to avoid the formation of metallic salt outside the reaction medium.

According to an embodiment of the invention, the process P further comprises an additional step after step S1) and before step S2) of maintaining the temperature of the reactor at a high temperature, preferably at a temperature ranging from 270° C. to 400° C., more preferably from 285 to 350° C., even more preferably from 300 to 350° C., until full conversion of fatty acid and disappearance of the optionally formed intermediate metallic salts.

According to an embodiment, the step S1) of the previous embodiment of the process P of the invention comprises the steps of:

S11) introducing at least part of the ketone K2 at liquid state, and at least part of the metal compound into a reactor, said reactor optionally containing, before said introduction, a part of the metal compound, a part of the fatty acid, fatty acid derivative or mixture thereof, a part of the ketone K2 and/or a part of the internal ketone K1, 512) introducing at least part of the fatty acid, fatty acid derivative or mixture thereof into said reactor, optionally with
a part of the metal compound and/or
a part of the intermediate metallic carboxylate salts obtained by reacting metal compound and fatty acid or fatty acid derivative or mixture thereof before decomposition to form the internal ketone K1.

According to an embodiment of the invention, all the ketone K2 may be introduced during step S11) and/or all the fatty acid or fatty acid derivative or mixture thereof may be introduced during step S12).

According to an embodiment wherein the fatty acid, fatty acid derivative or mixture thereof is mixed with the metal compound before introduction into the reaction medium, metallic carboxylate salts may be obtained by a reaction between metal compound and the fatty acid, fatty acid derivative or mixture thereof; said reaction can be carried out at a temperature lower than 270° C.

According to said embodiment, the ketone K2 and the metal compound introduced at step S11) may be introduced separately or together into the reactor. Indeed, the ketone K2 and the metal compound may be mixed outside the reactor, before their introduction into the reactor or the ketone K2 and the metal compound may be mixed into the reactor after their separate introduction into the reactor.

During step S11), at least part of the metal compound is also introduced into the reactor. According to an embodiment, the reactor initially comprises, before step S11), a part of the metal compound, for example, after implementation of step S12) (recovery of the synthetized ketones), a part of the metal compound remains in the reactor. According to another embodiment, all of the metal compound is introduced into the reactor during step S11).

According to an embodiment of process P, at step S11), the reactor is substantially free, in particular totally free, of fatty acid and fatty acid derivative. According to said embodiment, when the ketone K2 is introduced into the reactor, said reactor is substantially free of fatty acid and substantially free of fatty acid derivative.

During step S12), the fatty acid, fatty acid derivative or mixture thereof are introduced in the liquid state into the reactor containing the ketone K2 and the metal compound, for example through a funnel equipping the reactor. They may be added sequentially or continuously and they are profitably added at a rate avoiding the build-up of substantial amounts of free acid in the reaction system as well as significant temperature drop. The progress of the reaction and the conversion of the starting materials to the ketones K1 as final products may be conveniently monitored through appropriate methods like IR analysis.

During step S12), the fatty acid, fatty acid derivative or mixture thereof is generally added over a period of time which depends notably on the overall amount of acid or acid derivative used as well as the overall amount of metal compound present into the reactor.

Once the fatty acid derivative or fatty acid added in the process P of the invention has been converted, the desired internal ketone K1 can be easily recovered e.g. by distillation at reduced pressure. One can take also advantage of the ferromagnetic properties of the at least one metallic compound formed during the reaction (such as iron oxide(s)) to separate the metallic compound from the ketone by applying a magnetic field. Another way to separate the ketone from the metal compound is through a simple decantation or a simple filtration as the metallic compound is not soluble in the reaction mixture containing the ketone obtained as the reaction product. The skilled person is aware of representative techniques so that no further details need to be given here.

At step S2), the internal ketone K1 and the ketone K2 may be recovered together or separately, but preferably together. Indeed, according to a preferred embodiment of the invention, the ketone K2 and the internal ketone K1 are not separated.

The entire process P can be advantageously carried out under inert gas atmosphere and suitable inert gases are e.g. nitrogen or argon, to name only two examples.

The process P can also be done in a continuous way where iron oxides are separated off from the reaction product in another/third separation zone and the residue constituted mainly of iron oxide can be recycled back into the reactor. It has been found, that up to four cycles are possible without a significant loss of catalytic activity of the metal or metal compound.

In another embodiment of the process P, at the end of step S1) the metallic compounds are separated from the products, e.g. using conventional techniques, and then are recycled for the conversion of another batch of fatty acid or fatty acid derivative or mixture thereof preferably comprising at least 10 mol %, based on the entire amount of fatty acid and fatty acid derivative, of fatty acid having 12 carbon atoms or less or derivative of such fatty acid or mixture thereof.

In a same way, part of the ketones recovered at step S2) can be recycled in order to perform step S1) of the process P.

The yield of the desired ketones after step S1) normally exceeds 60%, more preferably 70% and can be as high as more than 90%.

According to an embodiment of the process P of the invention, the reaction medium in the reactor does not contain substantial amount of a third solvent. In a particularly preferred embodiment, no substantial amount of third solvent is added during the process P of the invention. For example, the reactor preferably comprises less than 5% by weight of third solvent(s), more preferably less than 3% by weight of third solvent(s), even more preferably less than 1% by weight of third solvent(s), based on the total weight of the reaction medium, ideally the reactor comprises no third solvent(s).

Within the meaning of the present invention, by the expression "third solvent", it is to be understood, a solvent different from the internal ketone K1, the ketone K2, the fatty acid or fatty acid derivative, the by-products that could be generated during the reaction.

Within the meaning of the present invention, the expression "reaction medium" refers to the medium, within the reactor, wherein the decarboxylative ketonization reaction takes place.

The reactor may be any kind of reactors that are conventionally used for the synthesis of ketones, in particular for the synthesis of ketones in liquid phase.

Within the meaning of the present invention, by "side reactions products", it is to be understood any product formed during the decarboxylative ketonization reaction different from ketones. Among side reaction products, mention may be made of hydrocarbons such as alkanes or alkenes.

The process P may be a continuous or a batch process.

In accordance with another embodiment, the process P of decarboxylative ketonization to the internal ketone K1 of formula (V) described above is characterized in that either a1) in a first step, elementary metal or a metal compound and the fatty acid, fatty acid derivative or mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5 (molar ratio metal:carboxyl group equivalent) and reacted for a period Pi of from 5 min to 24 h at a temperature $T_1$ of from 100° C. to 270° C. in the substantial absence of added solvent, and b1) thereafter the temperature is raised to a temperature $T_2$ which is strictly above 270° C. and up to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the substantial absence of added solvent until the molar ratio of fatty acid, fatty acid derivative or mixture thereof to metal is in the range of from 6:1 to 99:1, or a2) in a first step, elementary metal or a metal compound and the fatty acid, fatty acid derivative or mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5 (molar ratio metal:carboxyl group equivalent) and reacted for a period Pi of from 5 min to 24 h at a temperature $T_1$ which is strictly above 270° C. and strictly below 300° C. in the substantial absence of added solvent, and b2) thereafter the temperature is raised to a temperature $T_2$ which ranges from 300° C. to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the substantial absence of added solvent until the molar ratio of fatty acid, fatty acid derivative or mixture thereof to metal is in the range of from 6:1 to 99:1.

In accordance with the embodiment comprising steps a1) and b1) the following applies:

Temperature $T_1$

Temperature $T_1$ is of from 100° C. to 270° C.

Temperature $T_1$ is preferably of at least 180° C., more preferably of at least 210° C. and still more preferably of at least 230° C.

Besides, temperature $T_1$ may be of at most 260° C.

Temperature $T_1$ may be from 180° C. to 270° C. or from 210° C. to 260° C.

Good results were obtained when $T_1$ ranged from 230° C. to 270° C., in particular from 240° C. to 260° C.

Temperature $T_2$

Temperature $T_2$ is strictly above 270° C. and up to 400° C.

Temperature $T_2$ may be strictly below 280° C. However, it is preferably of at least 280° C., more preferably of at least 290° C. and still more preferably of at least 300° C. It may be strictly above 320° C.

Temperature $T_2$ may be strictly above 360° C. However, it is generally of at most 360° C. and often of at most 340° C. It may be of at most 320° C.

Temperature $T_2$ may be from 280° C. to 320° C. Temperature $T_2$ may also be strictly above 320° C. and up to 360° C.

Good results were obtained when $T_2$ ranged from 280° C. to 360° C., in particular from 300° C. to 340° C.

Difference of temperature $T_2$ minus $T_1$ ($T_2-T_1$)

Difference of temperature $T_2$ minus $T_1$ is advantageously of at least 3° C.

It is preferably of at least 10° C., more preferably of at least 30° C. and still more preferably of at least 45° C.

Besides, $T_2-T_1$ is advantageously of at most 100° C. It may be of at most at most 85° C., at most 70° C. or at most 55° C.

Good results were obtained when $T_2-T_1$ ranged from 30° C. to 100° C., in particular from 45° C. to 85° C.

Certain Combinations of Temperature $T_1$ and of Temperature $T_2$

In a first embodiment, $T_1$ is from 230° C. to 270° C., while $T_2$ is from 280° C. to 400° C., preferably from 290° C. to 360° C. and more preferably from 300° C. to 340° C.

In a second embodiment, $T_2$ is strictly below 280° C., while $T_1$ is from 180° C. to 270° C., preferably from 230° C. to 270° C. and more preferably from 240° C. to 260° C.

In a third embodiment, $T_2$ is from 280° C. to 320° C., while $T_1$ is from 180° C. to 270° C., preferably from 230° C. to 270° C. and more preferably from 240° C. to 260° C.

In a fourth embodiment, $T_2$ is strictly above 320° C. and up to 360° C., while
$T_1$ is from 180° C. to 270° C., preferably from 230° C. to 270° C. and more preferably from 240° C. to 260° C.

In a fifth embodiment, $T_2$ is strictly above 360° C., while $T_1$ is from 180° C. to 270° C., preferably from 230° C. to 270° C. and more preferably from 240° C. to 260° C.

Period of Time $P_1$

Period of time $P_1$ may vary to a large extent depending notably on the nature of the elementary metal or metal compound. In any case, period of time $P_1$ is from 5 min to 24 h.

Period of time $P_1$ is preferably of at least 10 min and more preferably of at least 20 min.

Besides, period of time $P_1$ is preferably of at most 12 h, more preferably of at most 8 h and still more preferably at most 5 h.

Good results were obtained with period of time $P_1$ of from 10 min to 8 h, in particular of from 20 min to 5 h.

Each specified lower limit, upper limit or range for period of time $P_1$ must be considered as explicitly described in combination with each specified lower limit, upper limit or range previously specified for temperature $T_1$.

Period of Time $P_2$

Period of time $P_2$ may also vary to a large extent depending notably on the overall amount of acid or acid derivative used. In any case, period of time $P_2$ is from 5 min to 24 h.

Period of time $P_2$ is preferably of at least 30 min, more preferably of at least 1 h and still more preferably of at least 2 h.

Besides, period of time $P_2$ is preferably of at most 16 h and more preferably of at most 8 h.

Good results were obtained with period of time $P_2$ of from 1 h to 16 h, in particular of from 2 h to 8 h.

Each specified lower limit, upper limit or range for period of time $P_2$ must be considered as explicitly described in combination with each specified lower limit, upper limit or range for temperature $T_2$.

In a certain embodiment of the process P:
temperature $T_1$ is from 180° C. to 270° C., preferably from 210° C. to 260° C.
period of time $P_1$ is from 5 min to 240 min, and
period of time $P_2$ is from 1 h to 24 h.

In accordance with the process P comprising steps a2) and b2) the following applies:

Temperature $T_1$

Temperature $T_1$ is strictly above 270° C. but is strictly below 300° C.

Temperature $T_1$ is preferably at least 275° C., more preferably at least 280° C. and still more preferably least 285° C.

Besides, temperature $T_1$ may be at most 295° C.

Temperature $T_1$ may be from 272° C. to 298° C. or from 275° C. to 295° C. Good results were obtained when $T_1$ ranged from 280° C. to 295° C., in particular from 285° C. to 295° C.

Temperature $T_2$

Temperature $T_2$ is in the range of from 300° C. to 400° C.

Temperature $T_2$ is preferably at least 305° C., more preferably at least 310° C.

Temperature $T_2$ is preferably at most 380° C., more preferably at most 360° C., and often at most 340° C. It may be at most 320° C.

Temperature $T_2$ in a first preferred embodiment $E_1$ (which is exemplified in Example 1) may be of from 320° C. to 360° C., even more preferably from 320° C. to 340° C.

The period $P_2$ is preferably of from 2 to 12 h, still more preferably of from 2 to 8 h.

The molar ratio of metal:carboxylate group equivalent in the first step is preferably in the range of from 1:1.0 to 1:3.0, even more preferably in the range of from 1:1.3 to 1:2.6.

In accordance with another embodiment, temperature $T_2$ is in the range of from 300 to 320° C., preferably in the range of from 305 to 310° C.

In such embodiment period $P_2$ is preferably of from 15 min to 18 h, still more preferably of from 30 min to 17 h and even more preferably of from 1 to 16 h.

Difference of Temperature $T_2$ Minus $T_1$ ($T_2-T_1$)

Difference of temperature $T_2$ minus $T_1$ is advantageously at least 3° C. It is preferably at least 5° C., more preferably at least 15° C.

Besides, $T_2-T_1$ is advantageously at most 100° C. It may be at most 80° C., at most 60° C. or at most 50° C.

Good results were obtained when $T_2-T_1$ ranged from 10° C. to 100° C., in particular from 15° C. to 80° C.

Period of Time $P_1$

Period of time $P_1$ may vary to a large extent depending notably on the nature of the elementary metal or metal compound and the temperature T1. In any case, period of time $P_1$ is from 5 min to 24 h.

Period of time $P_1$ is preferably of at least 10 min and more preferably of at least 20 min.

Besides, period of time $P_1$ is preferably at most 12 h, more preferably at most 8 h and still more preferably at most 6 h.

Good results were obtained with period of time $P_1$ of from 10 min to 8 h, in particular of from 20 min to 6 h.

Each specified lower limit, upper limit or range for period of time $P_1$ must be considered as explicitly described in combination with each specified lower limit, upper limit or range previously specified for temperature $T_1$.

Period of Time $P_2$

Period of time $P_2$ may also vary to a large extent depending notably on the overall amount of acid or acid derivative used and temperature $T_2$. In any case, period of time $P_2$ is from 5 min to 24 h.

Period of time $P_2$ is preferably of at least 15 min, more preferably of at least 1 h and still more preferably of at least 2 h.

Besides, period of time $P_2$ is preferably of at most 18 h and more preferably of at most 16 h.

Good results were obtained with period of time $P_2$ of from 1 h to 18 h, in particular of from 2 h to 15 h.

Each specified lower limit, upper limit or range for period of time $P_2$ must be considered as explicitly described in combination with each specified lower limit, upper limit or range for temperature $T_2$.

The following applies to the process in accordance with the present invention comprising process P with steps a1) and b1) or steps a2) and b2).

In the first step of the process P, elementary metal (or a mixture of elementary metals) or a metal compound (or a mixture of metal compounds) and the fatty acid, fatty acid derivative or mixture thereof comprising at least 10 mol %, based on the entire amount of fatty acid or fatty acid derivatives, of fatty acid having 12 carbon atoms or less or derivative of such fatty acid, are mixed in a molar ratio of from 1:0.8 to 1:3.5 (molar ratio metal:carboxylate group equivalent) and reacted for a period of time $P_1$ at a temperature $T_1$ in the substantial absence of added solvent, preferably in the absence of added solvent.

Suitable metals have been described herein before in connection with the description of the process P comprising the addition of an internal ketone K2 and reference is made thereto to avoid repetitions.

The same applies to the fatty acids and fatty acid derivatives which have also been described hereinbefore for the process P comprising the addition of a ketone K2. Those fatty acids and fatty acid derivatives are also suitable for the process P wherein a1) and b1) respectively a2) and b2) are applied.

It is understood that, when one and only one fatty acid or fatty acid derivative is used as the starting material, it must have 12 carbon atoms or less.

The fatty acids may comprise one or more double bonds in their chains. Examples of such fatty acids are oleic acid, linoleic acid, linolenic acid, erucic acid, palmitoleic acid and mixtures thereof.

The fatty acids may comprise one or more triple bonds in their chains. Examples of such fatty acids are tariric acid, santalbic acid and mixtures thereof.

The aliphatic groups of the fatty acids are generally chosen from alkyl, alkenyl, alkanedienyl, alkanetrienyl and alkynyl groups, preferably from alkyl and alkenyl groups, more preferably from alkyl groups.

During the first step of the process P in accordance with the present invention a metal carboxylate is formed as an intermediate species which in the subsequent step decomposes into the desired ketone and a metal oxide which is the active catalytic species for the subsequent conversion of the acid or acid derivative added sequentially or continuously in the second step to the desired ketone containing mixture.

If a metal is used in the first step, said metal reacts with the fatty acid to a carboxylate of the metal with simultaneous formation of hydrogen gas. If a metal oxide is used in the first step, the formation of the carboxylate is accompanied by the simultaneous formation of water. The overall equation for the carboxylate formation in the first step (for a metal having a valency of 2 as example) can be represented as follows:

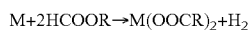

M+2HCOOR→M(OOCR)$_2$+H$_2$

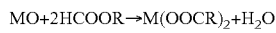

MO+2HCOOR→M(OOCR)$_2$+H$_2$O

The molar ratio of metal or metal compound to the total amount of carboxylic groups in the starting material in the first step is in the range of from 1:0.8 to 1:3.5 and it is generally preferred to use a molar ratio which is sufficient to form the respective metal carboxylate and to convert all the acid or acid derivative present to the metal carboxylate, i.e. basically leaving no free carboxylic groups after formation of the carboxylate after the first step. Thus, for a bivalent metal, the molar ratio of metal to carboxylic groups is preferably about 1:2 as two equivalents of acid groups are needed to form the metal dicarboxylate of a bivalent metal. If metal oxide compounds are used instead of elementary metal, the molar ratio referred to above is calculated with the amount of elementary metal in the oxide compound. The molar amount of carboxylic groups is calculated taking into account the number of such groups in the fatty acid or fatty acid derivative which is used as a starting material. Thus, for example an anhydride of an acid comprises two carboxylate functionalities and can provide two carboxylic groups for the formation of the metal carboxylate.

The formation of the metal carboxylate in the first step can be conveniently monitored by in situ IR analysis. The carbonyl absorption band of the acid is subject to a bathochromic shift in the metal carboxylate which allows the monitoring of the reaction progress.

In accordance with a particularly preferred embodiment of the process P, iron powder is used as metal as same is cheap and abundantly available.

Second Step of the Process P

In the second step of the process P comprising steps a1) and b1) respectively a2) and b2), the temperature is raised to temperature $T_2$ at which temperature the metal carboxylate decomposes advantageously to the desired ketone, metal oxide and carbon dioxide.

Additional fatty acid, fatty acid derivative or a mixture thereof comprising at least 10 mol %, based on the entire amount of fatty acid or fatty acid derivative, of fatty acid having 12 carbon atoms or less or derivative of such fatty acid is added in the second step, in the substantial absence of added solvent, preferably in the absence of added solvent. They may be added sequentially or continuously and they are profitably added at a rate avoiding the build-up of substantial amounts of free acid in the reaction system. Again, the progress of the reaction and the conversion of the starting materials to the carboxylates as intermediates and the ketones as final products may be conveniently monitored through appropriate methods like IR analysis.

During the second step, additional fatty acid, fatty acid derivative or a mixture thereof is added over a period of time $P_2$ which depends notably on the overall amount of acid or acid derivative used and the temperature.

For example, in one embodiment, period of time $P_2$ is in the range of from 15 min h to 18 h, preferably of from 1 h to 16 h and particularly preferably of from 2 to 15 hours.

The total amount of fatty acid material (fatty acid or fatty acid derivative) added in the second step of the reaction is such that the overall molar ratio of metal to the amount of carboxylic groups reached at the end of the second step is in the range of from 1:6 to 1:99, i.e. the amount of metal compound is about 1 mol % to about 14 mol % and preferably of from 2 to about 13 mol % of the entire amount of fatty acid or fatty acid derivative, i.e. the metal or metal compound truly functions in a catalytic manner and is not used up in the course of the reaction. For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P as used herein.

What has been said above for the composition of the starting fatty acid material in the first step of the process P also applies to the second step.

The process P is preferentially carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

The process P can be carried out in the substantial absence of added solvent, preferably in the absence of added solvent. The desired ketone formed during the reaction basically acts as a solvent for the reaction. Since the ketone formed generally as a higher boiling point than the fatty acid, fatty acid derivative or mixture thereof used as starting material, this allows to carry out the reaction in the liquid phase as desired without the addition of an external solvent which would have to be removed at the end of the reaction and which is cost and labour intensive and thus undesirable.

Period of time $P_{12}$

The additional fatty acid, fatty acid derivative or mixture thereof may be added over period of time $P_2$ under the above specified conditions immediately after the temperature has been raised to $T_2$ (which particular embodiment corresponds to $P_{12}$, as defined hereinafter, equal to 0).

Alternatively, after the temperature has been raised to $T_2$ and before the additional fatty acid, fatty acid derivative or mixture thereof is added over period of time $P_2$, said temperature may be maintained at temperature $T_2$ during a period of time $P_{12}$ (>0).

Period of time $P_{12}$ is preferably at least 30 min and more preferably at least 1 h.

Besides, period of time $P_{12}$ is preferably at most 5 h and more preferably at most 3 h.

Good results were notably obtained with $P_{12}$ ranging from 30 min to 300 min, especially from 1 h to 3 h.

Period of Time $P_{23}$

Immediately after the additional fatty acid, fatty acid derivative or mixture thereof has been added over period of time $P_2$, the temperature may be decreased, possibly down to a temperature $T_3$ which is preferably in the range of from about 5° C. to about 150° C. (which particular embodiment corresponds to $P_{23}$, as defined hereinafter, equal to 0). Temperature $T_3$ may preferably be the room temperature or a temperature slightly above the room temperature.

Alternatively, after the additional fatty acid, fatty acid derivative or mixture thereof has been added over period of time $P_2$, the temperature may be maintained at temperature $T_2$ during a period of time $P_{23}$ (>0).

Period of time $P_{23}$ is preferably at least 30 min and more preferably at least 1 h.

Besides, period of time $P_{23}$ is preferably at most 5 h and more preferably at most 3 h.

Good results were notably obtained when $P_{23}$ ranged from 30 min to 300 min, especially from 1 h to 3 h.

Recovery of the Fatty Acid Ketone and Recycling of Metallic Compounds

The internal ketone synthesized by the process P can be isolated. To this effect, conventional separation means, which are well known to the skilled person, can be used.

Thus, for example, once the fatty acid derivative or fatty acid added in the second step of the process P has been converted, the desired ketone can be easily obtained e.g. by distillation at reduced pressure. One can take also advantage of the ferromagnetic properties of the metallic compounds formed during the reaction (such as iron oxides) to separate the metallic compounds from the ketone by applying a magnetic field. Another way to separate the products ketone from the metal compounds is through a simple filtration as the metallic compounds are not soluble in the ketones obtained as reaction product. The skilled person is aware of representative techniques so that no further details need to be given here.

The entire process P can be advantageously carried out under inert gas atmosphere and suitable inert gases are e.g. nitrogen or argon, to name only two examples.

In accordance with another preferred embodiment, after separation of the desired ketone, the remaining residue constituted mainly of metallic compounds (for example the bottom material after distillation) can be directly reused for a second cycle of addition of fatty acid or fatty acid derivative to be converted to the desired fatty acid ketones. Overall, amounts of as low as one mole percent of metal or metal compound, relative to the amount of carboxylic acid equivalents is sufficient to obtain the desired ketones in good yield. It has been found, that up to four cycles are possible without a significant loss of catalytic activity of the metal or metal compound.

Accordingly, in another preferred embodiment of the process P, at the end of step b1) respectively b2) the metallic compounds are separated from the products using conventional techniques and then are recycled for the conversion of another batch of fatty acid or fatty acid derivative or a mixture thereof comprising at least 10 mol %, based on the entire amount of fatty acid or fatty acid derivative, of fatty acid having 12 carbon atoms or less or derivative of such fatty acid.

The yield of the desired ketones after step two normally exceeds 60 present, more preferably 70% and can be as high as more than 90%.

The quaternization reaction to which the tertiary amine of formula (VII) obtained in the first step of the process for the manufacture of compounds of formula (I) is subjected is a common reaction known to the skilled person which has been described in the literature. Alkylating agents are commonly used for this conversion and suitable examples for such alkylating agents are known to the skilled person so that no further details need to be given here. Suitable alkylating agents are e.g. alkyl halides and dialkyl sulfates, and dialkyl sulfates, in particular dimethyl sulfate, have shown to be particularly advantageous in certain cases.

The reaction is hereinafter described in more detail for dimethyl sulfate as an alkylating agent but the skilled person will adopt the reaction conditions accordingly if other alkylating agents are used based on his professional experience.

The reaction of the tertiary amine with the alkylating agent (e.g. dimethyl sulfate) is usually carried out in a solvent (e.g. polar organic solvents such as THF, methanol or 1,4-dioxane). THF and methanol have shown to be advantageous in certain cases. The use of a solvent is not mandatory, however, and the quaternization reaction may be carried out in the absence of added solvent. The triamine of formula (VII) and the alkylating agents are mixed in the appropriate stoichiometric amount (that is to say the necessary amount of alkylating agent to achieve quantitative quaternization of the two terminal amino groups (—$NR_1R_2$ and —$NR_3R_4$) in the compounds of formula (VII) or to achieve quantitative quaternization of the terminal —$NR_1R_2$ group in the compound of formula (VIII) (as defined hereinafter) at a temperature in the range from 15° C. to the boiling point of the solvent used (the reaction can be carried out under reflux) or up to 400° C. in case no solvent is used or in the case the reaction is conducted under pressure in an autoclave. The reaction time may last from 2 h to several days, depending on the amine used as starting material. Reaction progress can be monitored by NMR spectroscopy where residual amounts of dimethylsulfate can be traced and amine can be added to achieve a full conversion of the dimethyl sulfate, if needed. The dimethyl sulfate is usually added progressively, e.g. with a syringe or similar dosing system in a manner that the temperature of the system during the addition does not exceed 40° C. due to the exothermy of the reaction.

Once full conversion of the dimethyl sulfate is achieved, the solvent (if the reaction was carried out in a solvent) is usually evaporated (e.g. under vacuum) and the resulting crude product is preferably subjected to a heating step at reduced pressure to remove remaining traces of the alkylating agent and the solvent. The desired product, the quaternary ammonium compound of formula (I), is in many cases obtained in quantitative or near quantitative yields, i.e. in yields exceeding 90%, preferably exceeding 95% and preferably in yields of 98% or more.

The final product (the compound of formula (I)) can be characterized e.g. by NMR spectroscopy.

In accordance with another process in accordance with the present invention, compounds of formula (VIII)

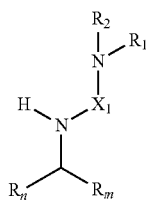

(VIII)

wherein $R_n$, $R_m$, $R_1$, $R_2$ and $X_1$ and $X_2$ have the meaning as defined in claim 1 are subjected to a quaternization reaction to obtain the compounds of formula (II), (III) or (IV). In many cases a mixture of compounds of formulae (II), (III) and (IV) is obtained from which the compounds of formula (II), (III) and (IV) may be isolated in an appropriate manner, if desired.

The compounds of formula (VIII) and processes for their manufacture have been described e.g. in WO 2017/174424 to which reference is made here for further details.

The compounds of formula (VIII) can be obtained by reacting an internal ketone of formula (V) with a diamine of formula (IX)

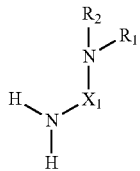

(IX)

under reductive amination conditions. The internal ketone can be obtained in accordance with a process P as described above or by a process as described in detail starting on page 8 of WO 2017/174424.

The conditions used for the quaternization reaction of compounds of formula (VIII) usually differ from the ones used for quaternization reaction of the compounds of formula (VII) due to the fact that the secondary amine group present in compounds of formula (VIII) can also react with the alkylating agent during the reaction thereby consuming a certain amount of alkylating agent. In addition, quaternization of this secondary amine group generates an ammonium group that can be seen as a "protonated amine" which can undergo proton exchange with the tertiary amine groups —$NR_1R_2$ present in the reaction mixture thereby preventing further quaternization at the tertiary amine groups. In order to achieve a satisfactory degree of quaternization at the tertiary amine group —$NR_1R_2$, it has been found advantageous to neutralize the ammonium after addition of the alkylating agent and to work with an excess of alkylating agent, e.g. 2 equivalents of alkylating agents with respect to the compound of formula (VII). This can e.g. be achieved by the addition of sodium carbonate in suitable amounts (usually appr. 1 molar equivalent of carbonate per secondary amine group). Further details are given in the working examples.

It is a last object of the present invention to provide new valuable compounds, with a particular interest for surfactants.

This last object of the present invention is achieved by a variety of compounds of formula (I), (II), (III) or (IV), notably surfactants, susceptible of being prepared by the methods as above described.

The compounds and compositions of the present invention have good surfactant properties and are suitable for a large number of different applications.

The adsorption properties of surfactants on negatively charged surfaces are important for a variety of applications and the compounds and compositions of the present invention show superior properties in this regard compared to respective products which have been described in the literature. To determine the adsorption properties on negatively charged surfaces, cellulose nanocrystals are commonly used as reference material. A suitable test is described in more detail in the working examples.

In addition the compounds in accordance with the present invention show a self-assembly into lamellar phases at low concentrations and a low critical micelle concentration.

One application for which the compounds in accordance with the present invention have been found beneficial is the use as floculants.

EXAMPLES

Synthesis of Compounds of Formula (I) Using Catalytic Reductive Amination Under $H_2$ Pressure This amination reaction is performed by reacting the ketone (V) and 3,3'-iminobis(N,N-dimethylpropylamine) in the presence of a transition metal (e.g. Ni, Co, Cu, Fe, Rh, Ru, Ir, Pd, Pt) based catalyst (typically Pd/C as one possibility), in an autoclave under hydrogen pressure (typically between 1 atm. and 200 bar).

The amine reactant can be used either in stoichiometric amounts, in excess or in sub-stoichiometric amounts relative to the amount of internal ketone.

The reaction can be carried out in a solvent. However, the presence of such a solvent is not compulsory and according to a specific embodiment, no solvent is used for this step. The exact nature of the solvent, if any, may be determined by the skilled person. Typical suitable solvents include, without limitation, water, methanol, ethanol, isopropanol, tert-butanol, THF, 2-methyltetrahydrofuran, 1,4-dioxane, dimethoxyethane, diglyme and mixtures thereof.

This reductive amination is usually carried out at a temperature ranging from 15° C. to 400° C. and may be conducted batch wise, semi-continuously or continuously and generally performed either in a batch mode or in a continuous mode using either a slurry or a fixed bed process (gas-solid or gas-liquid-solid process).

To improve yield and selectivity, generated water can be removed over the course of the reaction for example with a Dean-Stark apparatus using an appropriate solvent such as toluene. Water can also be trapped using for example molecular sieves.

Lewis or Bronsted acidic reactants (for example homogeneous $TiCl_4$, $AlCl_3$, $FeCl_3$, metal triflate compounds, or heterogeneous Amberlyst resins, Aquivion or Nafion Resins, zeolithes, silica-aluminas etc. . . . ) can also be used either in catalytic or stoichiometric amounts to improve yield and kinetics

Example 1 Synthesis of Triamine of Formula (VI) Using $C_{23}$ 12-Tricosanone as Starting Material In a 500 mL round bottom flask equipped with a condenser, a magnetic stirrer, a heater and a temperature probe were added:
  10 g of 023 ketone, 12-tricosanone (0.030 mole),
  13.8 g of 3,3'-iminobis(N,N-dimethylpropylamine) (0.074 mole)
  200 mL of dry THF The mixture was stirred at room temperature and 16.8 g of $Ti(OiPr)_4$ (0.059 mole) was added into the mixture.

The reaction medium was then stirred at 60° C. for 36 hours.

The mixture was then allowed to cool down at room temperature and 100 mL of methanol were added followed by the careful addition of 1.1 g of $NaBH_4$ (0.030 mole). During $NaBH_4$ addition, gas generation was observed causing some foaming.

The mixture was then stirred at room temperature during 4 h and 200 mL of water was then added causing precipitation of $TiO_2$.

200 mL of diethyl ether was then added into the reaction vessel and the suspension was filtered. The biphasic filtrate was then decanted and the organic phase was washed 3 times using a NaOH (0.5 M) aqueous solution. The organic phase was finally dried over $MgSO_4$, filtered and evaporated to give yellow oil.

The crude product was then purified by flash chromatography with an automated Combiflash apparatus using an eluent going from 100% $CH_2Cl_2$ (containing 1 wt % of $NEt_3$) to a mixture of $CH_2Cl_2$:MeOH (80:20 containing 1 wt % of $NEt_3$).

After collection of fractions and solvent evaporation, 4.7 g (0.009 mole) of pure product was obtained as a colorless oil corresponding to a yield of 32%.

Example 2—Synthesis of Triamine of Formula (VI) Using $C_{27}$ Heptacosan-14-One as Starting Material In a 2 liters double jacketed reactor equipped with a mechanical stirrer (propeller with four inclined plows), a temperature probe and a condenser were added:
  160 g of 027 ketone (0.405 mole)
  190 g of 3,3'-iminobis(N,N-dimethylpropylamine) (1.014 moles)
  500 mL of dry THF The mixture was stirred at room temperature and 230 g of $Ti(OiPr)_4$ (0.809 mole) was added into the reactor.

The mixture was then stirred at 65° C. (THF reflux) during 24 hours (it was observed that at this temperature the mixture became transparent→no suspension anymore).

The reaction mixture was then allowed to cool down to room temperature and 400 mL of methanol were added. Then 15.33 g of $NaBH_4$ (0.405 mole) was progressively added into the mixture. During $NaBH_4$ addition, gas release was observed.

The mixture was then stirred at room temperature during 4 hours.

300 mL of water was then added (precipitation of $TiO_2$ was observed) followed by 500 mL of diethyl ether.

The suspension was filtered in order to remove $TiO_2$ and the filtrate was decanted in order to separate organic phase and aqueous phase.

The organic phase obtained from filtrate was then washed 3 times with an aqueous NaOH [0.5M] solution, dried over $MgSO_4$, filtered and evaporated to afford 137 g of orange oil.

The oil was then purified by flash chromatography with automated Combiflash apparatus using an eluent going from 100% $CHCl_3$ (containing 3 wt % of $NEt_3$) to a mixture of $CHCl_3$:MeOH (75:25 containing 3 wt % of $NEt_3$).

4 clean fractions were collected and evaporated affording 82 g of oil (0.145 mole) of analytically pure compound (36% isolated yield, 43% selectivity when considering the unreacted ketone which has been recovered, 84% of ketone conversion).

Example 3—Synthesis of Triamine of Formula (VI) Using $C_{31}$ Hentriacontan-16-One as Starting Material In a 2 L double-jacketed reactor equipped with a mechanical stirrer (propeller with four inclined plows), a condenser and a temperature probe were added:
  25.3 g of hentriacontan-16-one (0.056 mole)
  26.1 g of 3,3'-iminobis(N,N-dimethylpropylamine) (0.139 mole)
  200 mL of dry THF The mixture was stirred at room temperature and 31.6 g of $Ti(OiPr)_4$ (0.111 mole) were added into the mixture. The mixture was then stirred at 65° C. (THF reflux) during 3 days. After cooling down to room temperature, 80 mL of dry methanol was added into the reactor vessel followed by the progressive addition of $NaBH_4$ (2.2 g, 0.057 mole) (foaming occurring during $NaBH_4$ addition).

The mixture was then stirred at room temperature during 4 hours and 200 mL of diethyl ether followed by 200 mL of water were added. During water addition $TiO_2$ precipitated as a white solid.

The mixture was filtered and the biphasic filtrate was decanted in order to recover the organic phase. The aqueous phase was extracted 3 times with 200 mL of diethyl ether, the organic fractions were collected and then washed 3 times with 200 mL of an aqueous NaOH solution (0.5 M).

The organic phase was dried over $MgSO_4$, filtered and evaporated to afford an orange oil.

As the $TiO_2$ solid filtered previously could have contained additional amounts of products, it was washed with 200 mL of ether followed by 500 mL of 80/20 mixture of $CHCl_3$/MeOH containing 2 wt % of $NEt_3$.

The obtained organic phase was then washed three times with 300 mL of an aqueous NaOH solution (0.5 M), dried over $MgSO_4$, filtered and evaporated. The obtained oil was combined with the previously recovered oil.

The crude oil was then purified by flash chromatography with automated Combiflash apparatus using an eluent going from 100% $CHCl_3$ (containing 2 wt % of $NEt_3$) to a mixture of $CHCl_3$:MeOH (75:25 containing 2 wt % of $NEt_3$).

6.44 g of the starting ketone containing 10 mol % of alcohol was recovered along with 11.12 g (0.018 mole) of the purified triamine corresponding to 32% isolated yield, 42% selectivity when considering the unreacted ketone which has been recovered, 77% of ketone conversion.

Example 4 Synthesis of Diamine of Formula (VIII) Using $C_{23}$ 12-Tricosanone as Starting Material In a 2 L double-jacketed reactor equipped with a mechanical stirrer (propeller with four inclined plows), a condenser and a temperature probe were added:
- 100.0 g of 12-tricosanone (0.295 mole)
- 60.4 g of dimethylaminopropylamine (DMAPA, 0.591 mole)
- 1 L of dry THF The mixture was stirred at room temperature and 67.3 g of Ti(OEt)$_4$ (0.295 mole) were added into the reactor vessel. The mixture was then allowed to stir (600 rpm) at room temperature during 20 hours and 250 mL of dry methanol was added into the reaction mixture followed by the progressive addition of 8.94 g (0.236 mole) of NaBH$_4$. During NaBH$_4$ addition some gas release along with foaming was usually observed during the solid addition.

After the end of NaBH$_4$ addition the mixture was allowed to stir at room temperature during 4 h and 300 mL of water were added followed by 300 mL of diethyl ether. During water addition formation of TiO$_2$ white precipitate was observed.

The white TiO$_2$ precipitate was removed by filtration and the biphasic filtrate was decanted in order to separate the organic phase and the aqueous phase. The organic phase was washed 3 times with 300 mL of a NaOH aqueous solution (2M), dried over MgSO$_4$, filtered and evaporated in order to afford 122.1 g of a crude pale yellow oil. At this stage the crude oil contained a by-product consisting of an adduct between the desired amine and BH$_3$. This adduct was transformed to the desired amine according to the following procedure:

The crude oil was dissolved in 200 mL of methanol and 12.2 g of Pd/C (3%) were added into the solution. The resulting mixture was allowed to stir at room temperature overnight. A slight exothermy along with generation of H$_2$ gas was observed. The slurry was then filtered in order to remove the solid catalyst and the filtrate was evaporated under vacuum to afford 118.5 g of analytically pure amine corresponding to 95% yield.

Example 5 Synthesis of Diamine of Formula (VIII) Using $C_{27}$ Heptacosanone as Starting Material In a 2 L double-jacketed reactor equipped with a mechanical stirrer (propeller with four inclined plows), a condenser and a temperature probe were added:
- 100.0 g of 14-heptacosanone (0.253 mole)
- 51.8 g of DMAPA (0.507 mole)
- 1 L of dry THF The mixture was stirred at room temperature and 57.8 g of Ti(OEt)$_4$ (0.253 mole) were added into the reactor vessel. The mixture was then allowed to stir (600 rpm) at room temperature during 20 hours and 250 mL of dry methanol were added into the reaction mixture followed by the progressive addition of 9.60 g (0.254 mole) of NaBH$_4$. During NaBH$_4$ addition some gas release along with foaming was usually observed during the solid addition.

After the end of NaBH$_4$ addition the mixture was allowed to stir at room temperature during 4 h and 200 mL of water were added followed by 300 mL of diethyl ether. During water addition formation of TiO$_2$ white precipitate was observed.

The white TiO$_2$ precipitate was removed by filtration and the biphasic filtrate was decanted in order to separate the organic phase and the aqueous phase. The organic phase was washed 3 times with 200 mL of a NaOH aqueous solution (1M), dried over MgSO$_4$, filtered and evaporated in order to afford 105.7 g of a crude pale yellow oil. At this stage the crude contained a by-product consisting of an adduct between the desired amine and BH$_3$. This adduct was transformed to the desired amine according to the following procedure:

The crude oil was dissolved in 100 mL of methanol and 10.0 g of Pd/C (3%) was added into the solution. The resulting mixture was allowed to stir at room temperature overnight. A slight exothermy along with generation of H$_2$ gas was observed. The slurry was then filtered in order to remove the solid catalyst and the filtrate was evaporated under vacuum to afford 100.3 g of analytically pure amine corresponding to 82% yield.

Example 6 Synthesis of Diamine of Formula (VIII) Using $C_{31}$ 16 Hentriacontan-16-One as Starting Material The same protocol as in Example 4 was used, except that $C_{23}$ 12-tricosanone was replaced by $C_{31}$ 16-hentriacontan-16-one. The desired amine was obtained in good yield and purity without the need to perform any flash chromatography on silica gel.

Examples 7 to 9 (Comparative)

Synthesis of an Amine of Formula (IX)

using $C_{23}$ 12-tricosanone as starting material

In a 250 mL round bottom flask equipped with a condenser, a magnetic stirrer, a heater and a temperature probe were added:
- 10 g of 12-tricosanone (0.03 mole)
- 37 mL of a dimethylamine solution in THF (2.0 M) (0.074 mole)
- 120 mL of dry THF The mixture was allowed to stir at room temperature and 16.8 g of Ti(OiPr)$_4$ (0.059 mole) were added into the reaction vessel. The mixture was then allowed to stir at room temperature during 20 h and 60 mL of ethanol were added followed by the progressive addition of 1.7 g of NaBH$_4$ (0.044 mole). During NaBH$_4$ addition some gas release along with foaming was observed during the solid addition. After the end of NaBH$_4$ addition, the mixture was then allowed to stir at room temperature during 4 h and 300 mL of water were added followed by the addition of 300 mL of CH$_2$Cl$_2$. Upon water addition, a white TiO$_2$ precipitate appeared.

The precipitate was filtered and the biphasic filtrate was decanted in order to separate the organic phase from the aqueous phase. The organic phase was washed 3 times with 300 mL of a NaOH aqueous solution (1M), dried over MgSO$_4$, filtered and evaporated in order to afford a crude pale yellow oil.

The crude product was then purified by flash column chromatography over silica gel using an eluent going from 100% $CH_2Cl_2$ to a mixture of $CH_2Cl_2$:MeOH (70:30) affording 6.9 g of a yellow oil corresponding to 64% isolated yield.

Example 8 Synthesis of an Amine of Formula (IX) Using $C_{27}$ 14-Heptacosanone as Starting Material In a 2 L double-jacketed reactor equipped with a mechanical stirrer (propeller with four inclined plows), a condenser and a temperature probe were added:
101.4 g of 14-heptacosanone (0.257 mole)
254 mL of a dimethylamine solution in THF (2.0 M) (0.508 mole)
700 mL of dry THF The mixture was stirred at room temperature and 115.6 g of $Ti(OEt)_4$ (0.507 mole) were added into the reactor vessel. The mixture was then allowed to stir (600 rpm) at 35° C. during 20 hours and 500 mL of dry methanol was added into the reaction mixture followed by the progressive addition of 9.84 g (0.260 mole) of $NaBH_4$. During $NaBH_4$ addition some gas release along with foaming was observed during the solid addition.

After the end of $NaBH_4$ addition the mixture was allowed to stir at room temperature during 4 h and 400 mL of water were added followed by 400 mL of diethyl ether. During water addition formation of $TiO_2$ white precipitate was observed.

The white $TiO_2$ precipitate was removed by filtration and the biphasic filtrate was decanted in order to separate the organic phase and the aqueous phase. The organic phase was washed 4 times with 500 mL of a NaOH aqueous solution (0.5 M), dried over $MgSO_4$, filtered and evaporated in order to afford 54 g of a crude viscous orange oil. At this stage the crude product contained a by-product consisting of an adduct between the desired amine and $BH_3$. This adduct was transformed to the desired amine according to the following procedure:

The crude oil was dissolved in a solvent mixture composed of 50 mL of methanol and 300 mL of isopropanol. 5.6 g of Pd/C (3%) were added into the solution and the resulting mixture was allowed to stir at room temperature overnight. A slight exothermy along with generation of $H_2$ gas was observed. The slurry was then filtered in order to remove the solid catalyst and the filtrate was evaporated under vacuum to afford 48.4 g of analytically pure amine corresponding to 45% yield.

Example 9 Synthesis of an Amine of Formula (IX) Using $C_{31}$ 16-Hentriacontanone as Starting Material In a 2 L double-jacketed reactor equipped with a mechanical stirrer (propeller with four inclined plows), a condenser and a temperature probe were added:
70.0 g of 16-hentriacontanone (0.155 mole)
155 mL of a dimethylamine solution in THF (2.0 M) (0.508 mole)
1 L of dry THF The mixture was stirred at room temperature and 70.9 g of $Ti(OEt)_4$ (0.311 mole) were added into the reactor vessel. The mixture was then allowed to stir (600 rpm) at room temperature during 20 hours and 350 mL of dry methanol were added into the reaction mixture followed by the progressive addition of 5.9 g (0.155 mole) of $NaBH_4$. During $NaBH_4$ addition some gas release along with foaming was observed during the solid addition.

After the end of $NaBH_4$ addition the mixture was allowed to stir at room temperature during 4 h and 300 mL of water were added. During water addition formation of $TiO_2$ white precipitate was observed. The white $TiO_2$ precipitate was filtered and washed with 150 mL of THF followed by two times with 500 mL of diethyl ether. The biphasic filtrate was concentrated under vacuum. 300 mL of diethyl ether were added into the residue and the obtained biphasic medium was decanted in order to separate the organic phase and the aqueous phase. The organic phase was washed 2 times with 250 mL of a NaOH aqueous solution (1 M), dried over $MgSO_4$, filtered and evaporated in order to afford 33.1 g of a crude orange paste. At this stage the crude product contained a by-product consisting of an adduct between the desired amine and $BH_3$. This adduct was transformed to the desired amine according to the following procedure:

The crude paste was dissolved in a solvent mixture composed of 180 mL of methanol and 100 mL of THF. 3.3 g of Pd/C (3%) were added into the solution and the resulting mixture was allowed to stir at room temperature overnight. A slight exothermy along with generation of $H_2$ gas was observed. The slurry was then filtered in order to remove the solid catalyst and the filtrate was evaporated under vacuum to afford 32.5 g of analytically pure amine corresponding to 44% yield.

Example 10—Synthesis of a Compound of Formula (I) Using the Amine Obtained in Example 1 as Starting Material In a 1 L double-jacketed reactor equipped with a mechanical stirrer (propeller with four inclined plows), a condenser and a temperature probe were added:
70.0 g of the triamine obtained in Example 1 (0.138 mole)
320 ml of dry THF The mixture was allowed to stir (600 rpm) at room temperature and 34.7 g of $Me_2SO_4$ (0.275 mole) were progressively added into the solution (40 minutes of addition) using a syringe so that the temperature of the reaction mixture did not exceed 40° C.

The mixture was then stirred overnight at room temperature and the reaction progress was monitored by NMR analysis. As long as $Me_2SO_4$ residual was still present in the reaction mixture a slight excess of the starting triamine was added in order to achieve full conversion of $Me_2SO_4$. The solvent was then evaporated under vacuum and the crude oil was subjected to heating at 80° C. under 5 mbar during 5 hours in order to remove traces of $Me_2SO_4$ and solvent.

105.6 g of the final product was obtained as an orange paste corresponding to a quantitative yield.

Example 11—Synthesis of a Compound of Formula (I) Using the Amine Obtained in Example 2 as Starting Material In a 250 mL double-jacketed reactor equipped with a mechanical stirrer (propeller with four inclined plows), a condenser and a temperature probe were added:
23.0 g of the triamine obtained in Example 2 (0.041 mole)
100 ml of dry THF.

The mixture was allowed to stir (600 rpm) at room temperature and 10.3 g of $Me_2SO_4$ (0.082 mole) were progressively added into the solution (20 minutes of addition) with a syringe so that the temperature of the reaction mixture did not exceed 40° C.

The mixture was then stirred overnight at room temperature and the reaction progress was monitored by NMR analysis. As long as $Me_2SO_4$ residual was still present in the reaction mixture a slight excess of the starting triamine was added in order to achieve full conversion of $Me_2SO_4$. The solvent was then evaporated under vacuum and the crude oil was subjected to heating at 80° C. under 5 mbar during 5 hours in order to remove traces of $Me_2SO_4$ and solvent.

33.2 g of the final product was obtained as an orange paste corresponding to a 99% isolated yield.

Example 12—Synthesis of a Compound of Formula (I) Using the Amine Obtained in Example 3 as Starting Material In a 250 mL double-jacketed reactor equipped with a mechanical stirrer (propeller with four inclined plows), a condenser and a temperature probe were added:
  40.0 g of the triamine obtained in Example 3 (0.064 mole)
  170 ml of dry THF.

The mixture was allowed to stir (600 rpm) at room temperature and 16.23 g of $Me_2SO_4$ (0.129 mole) were progressively added into the solution (20 minutes of addition with a syringe so that the temperature of the reaction mixture did not exceed 40° C.

The mixture was then stirred overnight at room temperature and the reaction progress was monitored by NMR analysis. As long as $Me_2SO_4$ residual was still present in the reaction mixture a slight excess of the starting triamine was added in order to achieve full conversion of $Me_2SO_4$. The solvent was then evaporated under vacuum and the crude oil was subjected to heating at 80° C. under 5 mbar during 5 hours in order to remove traces of $Me_2SO_4$ and solvent.

55.2 g of the final product is obtained as an orange paste corresponding to a 98.2% isolated yield.

Example 13—Synthesis of a Mixture of Compounds (II), (III) and (IV) from the Diamine Obtained in Example 4

In a 250 mL double-jacketed reactor equipped with a mechanical stirrer (propeller with four inclined plows), a condenser and a temperature probe were added:
  33.0 g of the diamine obtained in Example 4 (0.078 mole)
  160 ml of dry THF.

The mixture was allowed to stir (600 rpm) at room temperature and 19.6 g of $Me_2SO_4$ (0.155 mole) were progressively added into the solution (20 minutes of addition) with a syringe so that the temperature of the reaction mixture did not exceed 40° C.

The mixture was then stirred at room temperature during 2 h and 8.23 g of $Na_2CO_3$ (0.078 mole) was added into the reactor vessel. The reaction mixture was then allowed to stir at room temperature overnight. The reaction progress was followed by NMR. As long as $Me_2SO_4$ residual was still present in the reaction mixture, a slight excess of the starting diamine was added in order to achieve full conversion of $Me_2SO_4$. The mixture was then filtered in order to remove insoluble salts and the solid was washed with THF. The solvent was removed under vacuum.

The crude oil was subjected to an additional heating at 80° C. under 5 mbar during 5 hours in order to remove traces of $Me_2SO_4$ and solvent.

46.5 g of final product was obtained as a beige paste corresponding to a quantitative isolated yield. NMR analysis showed that the product consisted actually in an ammonium compounds mixture of three compounds represented by formulae II, III and IV composed of
  19 mol % of the compound of formula III
  44 mol % of the compound of formula IV
  37 mol % of the compound of formula II

Example 14—Synthesis of a Mixture of Compounds (II), (III) and (IV) from the Diamine Obtained in Example 5

In a 1 L double-jacketed reactor equipped with a mechanical stirrer (propeller with four inclined plows), a condenser and a temperature probe were added:
  90.0 g of the diamine obtained in Example 5 (0.187 mole)
  350 ml of dry THF The mixture was allowed to stir (600 rpm) at room temperature and 47.2 g of $Me_2SO_4$ (0.374 mole) were progressively added into the solution (20 minutes of addition) with a syringe so that the temperature of the reaction mixture did not exceed 40° C.

The mixture was then stirred at room temperature during 2 h and 39.68 g of $Na_2CO_3$ (0.374 mole) were added into the reactor vessel. The reaction mixture was then allowed to stir at room temperature overnight. The reaction progress was followed by NMR. As long as $Me_2SO_4$ residual was still present in the reaction mixture, a slight excess of the starting diamine was added in order to achieve full conversion of $Me_2SO_4$. The mixture was then filtered in order to remove insoluble salts and the solid was washed with methanol and THF. The solvent was removed under vacuum.

The crude oil was subjected to an additional heating at 80° C. under 5 mbar during 5 hours in order to remove traces of $Me_2SO_4$ and solvent.

123.7 g of final product was obtained as an orange paste corresponding to a quantitative isolated yield. NMR analysis showed that the product consisted actually in an ammonium compounds mixture of three compounds represented by formulae II, III and IV composed of
  14 mol % of the compound of formula III
  53 mol % of the compound of formula IV
  32 mol % of the compound of formula II.

Example 15—Synthesis of a Mixture of Compounds (II), (III) and (IV) from the Diamine Obtained in Example 6

The same protocol as in Example 14 was followed and a mixture of three compounds corresponding to formulae (II), (III) and (IV) was obtained. Their molar ratio was as follows:
  10 mol % of the compound of formula (II)
  20 mol % of the compound of formula (III)V
  70 mol % of the compound of formula (IV).

Example 16—Synthesis of a Quaternary Ammonium Compound Using the Amine of Example 7 as Starting Material In a 250 mL double-jacketed reactor equipped with a mechanical stirrer (propeller with four inclined plows), a condenser and a temperature probe were added:
  20.0 g of the amine obtained in Example 7 (0.054 mole)
  90 ml of dry THF.

The mixture was allowed to stir (600 rpm) at room temperature and 6.85 g of $Me_2SO_4$ (0.054 mole) were progressively added into the solution (20 minutes of addition) with a syringe so that the temperature of the reaction mixture did not exceed 40° C.

The mixture was then stirred at reflux (65° C.) during 3 h and the reaction progress was monitored by NMR analysis. As long as $Me_2SO_4$ residual was still present in the reaction mixture a slight excess of the starting amine was added in order to achieve full conversion of $Me_2SO_4$. The solvent was then evaporated under vacuum and the crude oil was subjected to an additional heating at 80° C. under 5 mbar during 5 hours in order to remove traces of $Me_2SO_4$ and solvent. 26.5 g of the final product was obtained as white solid corresponding to 98.5% isolated yield.

Example 17—Synthesis of a Quaternary Ammonium Compound Using the Amine of Example 8 as Starting Material In a 250 mL double-jacketed reactor equipped with a mechanical stirrer (propeller with four inclined plows), a condenser and a temperature probe were added:
48.7 g of the amine obtained in Example 8 (0.115 mole)
220 ml of dry THF.

The mixture was allowed to stir (600 rpm) at room temperature and 14.5 g of $Me_2SO_4$ (0.115 mole) were progressively added into the solution (20 minutes of addition) with a syringe so that the temperature of the reaction mixture did not exceed 40° C.

The mixture was then stirred at room temperature overnight and the reaction progress was monitored by NMR analysis. As long as $Me_2SO_4$ residual was still present in the reaction mixture a slight excess of the starting amine was added in order to achieve full conversion of $Me_2SO_4$. The solvent was then evaporated under vacuum and the crude oil was subjected to an additional heating at 80° C. under 5 mbar during 5 hours in order to remove traces of $Me_2SO_4$ and solvent. 61.9 g of the final product were obtained as orange solid corresponding to 98.0% isolated yield.

Example 18—Synthesis of a Quaternary Ammonium Compound Using the Amine of Example 9 as Starting Material In a 500 mL double-jacketed reactor equipped with a mechanical stirrer (propeller with four inclined plows), a condenser and a temperature probe were added:
40.3 g of the amine obtained in Example 9 (0.084 mole)
180 ml of dry THF.

The mixture was allowed to stir (600 rpm) at room temperature and 10.6 g of $Me_2SO_4$ (0.0.084 mole) were progressively added into the solution (20 minutes of addition) with a syringe so that the temperature of the reaction mixture did not exceed 40° C.

The mixture was then stirred at room temperature overnight and the reaction progress was monitored by NMR analysis. As long as $Me_2SO_4$ residual was still present in the reaction mixture a slight excess of the starting amine was added in order to achieve full conversion of $Me_2SO_4$. The solvent was then evaporated under vacuum and the crude oil was subjected to an additional heating at 80° C. under 5 mbar during 5 hours in order to remove traces of $Me_2SO_4$ and solvent. The final product was obtained as a beige paste with a quantitative isolated yield.

Example 19—Evaluation of Adsorption Properties of Quaternary Ammonium Compounds on Nanocellulose Crystals The adsorption of a cationic surfactant on negatively charged surfaces is an important property for surfactant. This property is usually linked to the minimal concentration of surfactant needed to produce aggregation of a negatively charged cellulose nanocrystal (CNC, which is often used as reference material)) suspension in aqueous media. Consecutive variation of size can be monitored and followed by dynamic light scattering.

Following the protocol described in E. K. Oikonomou et al., "Fabric Softener-Cellulose Nanocrystal interaction: A Model for assessing Surface Deposition on Cotton", J. Phys. Chem. B, 2017, 121 (10), 2299-307, the adsorption properties of the quaternary ammonium compounds were investigated by monitoring the ratio X=[surfactant]/[CNC] or the mass fraction M=[surfactant]/([surfactant+[CNC]), at fixed [surfactant]+[CNC]=0.01 wt % in aqueous solution, required to induce the agglomeration of the cellulose nanocrystals.

The results of the measurements are given in Table 1. A lower value for X or M indicates better adsorption properties on negatively charged surfaces.

TABLE 1

| Ex No. | Cpd. of ex. | Range X of CNC aggregation (Ratio X) $X_{min}$ to $X_{max}$ | Range X of CNC aggregation (Mass fraction M) $M_{min}$ to $M_{max}$ |
|---|---|---|---|
| 1C | Fentacare ® TEP | 1-20 | 50-95 |
| 2C | 16 | 0.1-2 | 9-66 |
| 3 | 11 | 0.02-1 | 2-50 |
| 4 | 13 | 0.1-2 | 8-66 |
| 5 | 14 | 0.1-2 | 8-50 |

[1] Fentacare ® TEP 88 was used, which is Di-(Palm-Carboxyethyl) Hydroxyethyl Methylsulfate Quaternary Ammonium Salt (CAS No 91995-81-2). The product is commercially available from various suppliers.

For the compounds in accordance with the present invention the aggregation of the cellulose nanocrystals occurred at a lower ratio $X_{min}$ of 0.1, 0.02 and 0.09 respectively, which is lower than the benchmark Fentacare® TEP where $X_{min}$ was determined to 1.0. Furthermore, aggregation with the compound mixtures of Examples 13 and 14 occurred at a lower ratio than for the compound of Example 16. These data show that the compound mixtures in accordance with the present invention show an improved adsorption on nanocellulose crystals.

Size distribution by intensity of aggregates obtained after CONTIN algorithms of dynamic light scattering (DLS) as described in E. K. Oikonomou et al., "Fabric Softener-Cellulose Nanocrystal interaction: A Model for assessing Surface Deposition on Cotton", J. Phys. Chem. B, 2017, 121 (10), 2299-307, was also determined.

The size distribution for pure CNC in water at 0.01 wt % gave a signal around 120 nm. With Fentacare® TEP no aggregation could be seen at a value X=0.5; the formation of high size aggregates started at a value of X=1 and even at a value of X=20, the formation of large size aggregates was observed.

A pure solution of Fentacare® TEP at 0.01 wt % in water also gave an aggregate size of 120 nm.

A solution of the pure compound of Example 11 gave a signal around 5 nm. At X=0.01, the signal of added CNC was observed without further CNC aggregation. Aggregation with the formation of large objects started at X=0.02 and was still visible at X=0.2. At a value X=1 almost no more aggregation was observed. At a value X=5 the size distribution was similar to the pure CNC alone at 0.01 wt % and no additional aggregation effect was observed.

The phases in the phase diagrams were investigated by the water penetration experiment. About 100 mg of each sample was taken on a slide and pressed to a thin film with coverslip, then the water droplet diffused form the outside of the sample film to the inside and afforded the concentration gradient. Photos were obtained of the concentration gradient under microscope with cross polarized light as obtained from the water penetration experiment.

These penetration experiments afforded the following information:

For the compounds of examples 11 and 12 a phase sequence isotropic phase→nematic phase→cubic phase→hexagonal phase→cubic phase→lamellar phase was observed. For the compound mixtures of Examples 13, 16 and 18 as well as for Fentacare® TEP 88 the phase sequence was isotropic phase→lamellar phase.

To define the boundary of the different phases in the phase diagrams, the surfactant samples with concentrations of 5 to 95 wt % were prepared in the glass tube and sealed. Then the sample was mixed, heated to 80° C. for one hour and then centrifuged for homogenization. The phase type was determined with a microscope with cross polarized light.

The invention claimed is:

1. A compound of general formula (I)

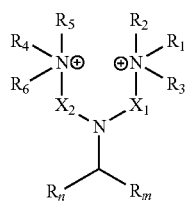

(I)

wherein $R_n$ and $R_m$ independently represent a $C_3$-$C_{27}$ alkyl group, $R_1$ to $R_6$, which may be the same or different at each occurrence, represent hydrogen or a $C_1$-$C_8$ alkyl group or wherein a pair of substituents selected from $R_1$, $R_2$ and $R_3$ in formula (I) or from $R_4$, $R_5$ and $R_6$ in formula (I), optionally form a divalent hydrocarbon radical with 2 to 6 carbon atoms thereby forming a ring structure with the nitrogen atom to which they are attached, wherein at least one of $R_1$ to $R_6$ is a methyl group, and $X_1$ and $X_2$, which are the same or different at each occurrence, represent a linear or branched divalent hydrocarbon radical with 1 to 24 carbon atoms which can be optionally substituted and/or interrupted by one or more heteroatoms or heteroatom containing groups.

2. The compound of formula (I) in accordance with claim 1, wherein $X_1$ and $X_2$ are —$(CH_2)_m$— with m being an integer equal to 2 to 20 and $R_1$ to $R_6$ are hydrogen or an alkyl group with 1 to 6 carbon atoms.

3. The compound in accordance with claim 2 wherein $X_1$ and $X_2$ are —$(CH_2)_3$— and $R_1$ to $R_6$ are methyl.

4. The compound of formula (I) in accordance with claim 1, wherein $X_1$ and $X_2$ are a branched divalent hydrocarbon group, which may be optionally substituted and/or interrupted by one or more heteroatoms or heteroatom containing groups and $R_1$ to $R_6$ are as defined.

5. The compound of formula (I) in accordance with claim 1, wherein $X_1$ and $X_2$ are a branched or linear divalent hydrocarbon group containing 2 to 20 carbon atoms substituted and/or interrupted by one or more heteroatoms or heteroatom containing groups and $R_1$ to $R_6$ are as defined.

6. The compound of formula (I) in accordance with claim 1, wherein $X_1$ and $X_2$ are a divalent aliphatic group containing 2 to 20 carbon atoms with the exception of —$(CH_2)_3$— and $R_1$ to $R_6$ are as defined.

7. The compound of formula (I) in accordance with claim 1, wherein $X_1$, $X_2$, $R_n$, and $R_m$ are as defined in claim 1 and $R_1$ to $R_6$ are a $C_2$-$C_8$ alkyl group.

8. A process for the preparation of a compound of formula (I) as defined in claim 1, the process comprising reacting an internal ketone K1 of formula (V), which can be obtained by a process P of decarboxylative ketonization, with a twin-tail amine of formula (VI) under reductive amination conditions to obtain a twin tail triamine of formula (VII) in accordance with the following general reaction scheme

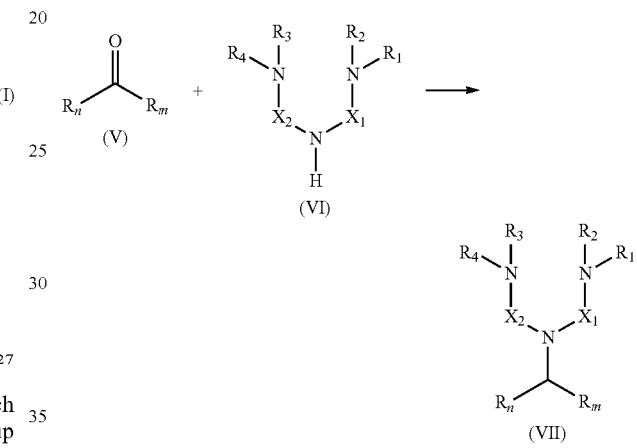

wherein $R_n$, $R_m$, $R_1$ to $R_4$, $X_1$ and $X_2$ have the meaning as defined in claim 1 in a first step, followed by a second step in which the reaction product obtained in the first step is quaternized to obtain the bicationic quaternary ammonium salt of formula (I).

9. The process of claim 8, wherein in the second step, the twin-tail triamine of formula (VII) is reacted with a dialkylsulfate wherein the alkyl groups in the dialkylsulfate have from 1 to 8 carbon atoms.

10. The process in accordance with claim 8, further comprising a step wherein the internal ketone K1 of formula (V) is synthesized by a process P of decarboxylative ketonization reaction of a fatty acid, a fatty acid derivative or a mixture thereof in a liquid phase with a metal compound as catalyst in a reaction medium, said process P being characterized in that a ketone K2 at liquid state, which is identical or similar to the internal ketone K1, is introduced into the reaction medium.

11. The process of claim 9, wherein the dialkylsulfate is dimethyl sulfate.

* * * * *